United States Patent
Tsukiji et al.

(10) Patent No.: US 10,557,704 B2
(45) Date of Patent: Feb. 11, 2020

(54) NON-DESTRUCTIVE DETECTION METHOD

(71) Applicant: DISCO CORPORATION, Tokyo (JP)

(72) Inventors: Shuichiro Tsukiji, Tokyo (JP); Yuki Ikku, Tokyo (JP); Keiji Nomaru, Tokyo (JP); Satoshi Kobayashi, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 0 days.

(21) Appl. No.: 16/265,353

(22) Filed: Feb. 1, 2019

(65) Prior Publication Data

US 2019/0242694 A1 Aug. 8, 2019

(30) Foreign Application Priority Data

Feb. 7, 2018 (JP) .................................. 2018-019941

(51) Int. Cl.
*G01B 11/22* (2006.01)

(52) U.S. Cl.
CPC .......... *G01B 11/22* (2013.01); *G01B 2210/56* (2013.01)

(58) Field of Classification Search
CPC ................ G01B 11/22; G01B 2210/56; G01N 21/9501; G01N 21/956; G01N 2201/068
USPC .................................................. 356/600–640
See application file for complete search history.

(56) References Cited

FOREIGN PATENT DOCUMENTS

| JP | 2002192370 A | 7/2002 |
|----|--------------|--------|
| JP | 2017166961 A | 9/2017 |

*Primary Examiner* — Tri T Ton
(74) *Attorney, Agent, or Firm* — Greer Burns & Crain Ltd.

(57) ABSTRACT

A non-destructive detection method includes, after carrying out a preparation step of preparing an inspection apparatus, an image acquisition step of intermittently moving an objective lens by a predetermined distance in a Z-axis direction orthogonal to an X-Y plane to be made closer to a first surface, positioning a focal point to a Z-axis coordinate value where a distance of the focal point extends by a refractive index of a workpiece, acquiring an X-Y plane image of an inside of the workpiece for each of a plurality of Z-axis coordinate values, and then, recording the acquired images in a recording unit, and a modified layer detecting step of detecting a state of a modified layer from the X-Y plane image for each of the plurality of Z-axis coordinate values recorded in the recording unit.

3 Claims, 5 Drawing Sheets

NON-DESTRUCTIVE DETECTION METHOD

BACKGROUND OF THE INVENTION

Field of the Invention

The present invention relates to a detection method of detecting a modified layer which is formed inside a workpiece by laser processing.

Description of the Related Art

There is a dividing method in which a wafer formed with a device in each of regions demarcated by a plurality of crossing division lines on a front side of the wafer is irradiated with a laser beam of a wavelength transmissible through the wafer to form a modified layer at a focal point where the laser beam is focused inside the wafer, and the wafer is divided with the modified layer as a starting point (see Patent Document No. Japanese Patent No. 3408805, for example).

In a technique of dividing a wafer, a depth position of a modified layer in a thickness direction of a wafer and a length of the modified layer are also related to an ease of division of the wafer. Accordingly, grasping the depth position and the length of the modified layer enables decision that a modified layer most suitable for dividing is formed. In view of this, Japanese Patent Laid-Open No. 2017-166961, for example, proposes a detection apparatus and a detection method in which an end portion of a wafer is cut in advance, after which a modified layer is formed inside the wafer, and then, a cut section is imaged from a side of a side surface of the wafer, whereby a state of the modified layer is observed.

SUMMARY OF THE INVENTION

In the invention disclosed in Japanese Patent Laid-Open No. 2017-166961, however, it is required to divide the end portion of the wafer in advance in order to image the modified layer, it takes time for observation. In addition, it is difficult to repetitively carry out formation of the modified layer and observation thereof, and accordingly, it is difficult to find an appropriate laser processing condition quickly.

It is therefore an object of the present invention to provide a non-destructive detection method which can select the most suitable laser processing condition for forming a desired modified layer by repetitively carrying out formation of a modified layer and observation thereof.

In accordance with an aspect of the present invention, there is provided a non-destructive detection method of detecting, in a non-destructive manner, a modified layer formed by positioning, inside a workpiece having a first surface and a second surface opposite to the first surface, a focal point of a laser beam of a wavelength transmissible through the workpiece and applying the laser beam to the workpiece. The non-destructive detection method includes a preparing step of preparing an inspection apparatus including imaging means provided with an objective lens and imaging the workpiece from a side of the first surface, a light source emitting light of a wavelength band transmissible through the workpiece from the side of the first surface, driving means causing the objective lens to move close to or apart from the first surface, and recording means recording an image imaged by the imaging means, an image acquisition step of, in a case in which the first surface is set as an X-Y plane, intermittently moving the objective lens by a predetermined distance H in a Z-axis direction orthogonal to the X-Y plane to be made closer to the first surface, positioning the focal point to each of a plurality of Z-axis coordinate values where a distance of the focal point extends by a refractive index of the workpiece, acquiring an X-Y plane image of an inside of the workpiece for each of the plurality of Z-axis coordinate values, and then, recording the acquired images in the recording means, and a modified layer detecting step of detecting a state of the modified layer from the X-Y plane image for each of the plurality of Z-axis coordinate values recorded in the recording means.

Preferably, in the modified layer detecting step, a three-dimensional image may be produced from the X-Y plane image for each of the plurality of Z-axis coordinate values recorded in the recording means, and from a two-dimensional image appearing in a cross-section where the modified layer is cut in a direction parallel to the Z-axis direction, a depth position of the modified layer in the Z-axis direction and a shape of the modified layer may be detected as the state of the modified layer.

Preferably, the workpiece may be a silicon wafer having a refractive index of 3.6, and in the image acquisition step, the distance of the focal point which extends inside the workpiece with respect to the predetermined distance H at which the objective lens intermittently moves in the Z-axis direction may be at least $3.6 \cdot H$, and the focal point intermittently may move by $3.6 \cdot H$ inside the workpiece.

According to the present invention, it is possible to detect the state of the modified layer formed inside the workpiece in a non-destructive manner. Thus, according to the present invention, it is possible to repetitively carry out formation of the state of the modified layer by laser processing and detection of the state of the modified layer by the imaging means, thereby quickly selecting the most suitable laser processing condition for the formation of the modified layer.

In the modified layer detecting step, since the three-dimensional image is produced from the X-Y plane image for each of the plurality of Z-axis coordinate values recorded in the recording means, and from the two-dimensional image appearing in the cross-section where the modified layer is cut in the direction parallel to the Z-axis direction in the three-dimensional image, the depth position of the modified layer in the Z-axis direction and the shape of the modified layer are detected as the state of the modified layer, the entire shape of the modified layer can be grasped even in a state in which the workpiece is not destructed, so that the state of the modified layer can be detected with high precision.

Preferably, the workpiece is a silicon wafer having a refractive index of 3.6, and in the image acquisition step, the distance of the focal point which extends inside the workpiece with respect to the predetermined distance H at which the objective lens intermittently moves in the Z-axis direction is at least $3.6 \cdot H$, and the focal point intermittently moves by $3.6 \cdot H$ inside the workpiece, the state of the modified layer can be detected even in a state in which the workpiece is not destructed.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

Figure 1:
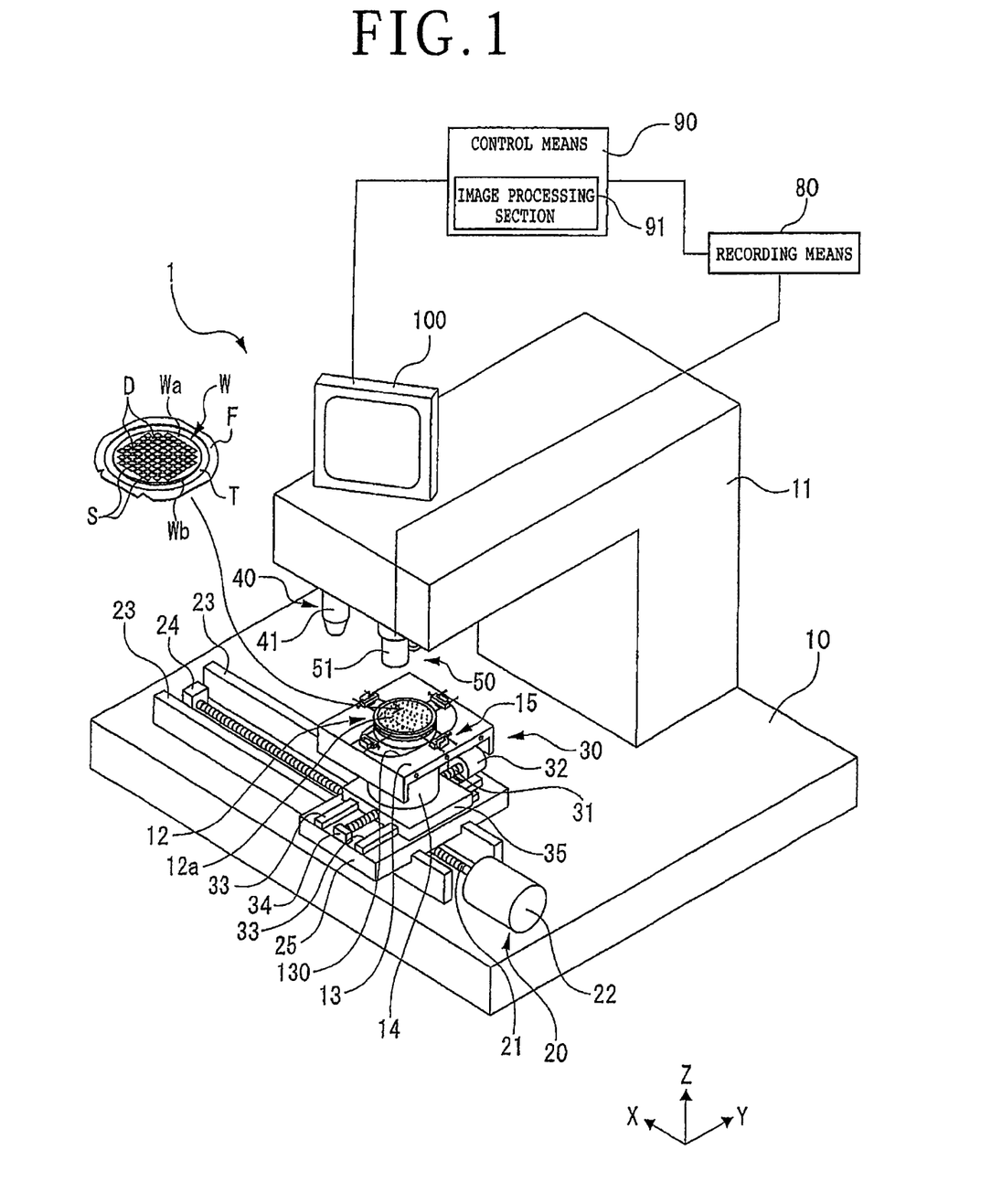
FIG. 1 is a perspective view illustrating a configuration of one example of a detection apparatus.

A workpiece W illustrated in FIG. 1 has a substrate having a circular disc-shape, for example, and on a front surface (a first surface Wa in the figure) of the workpiece W, a plurality of devices D are individually formed into a plurality of regions demarcated by a plurality of division lines S formed in a grid pattern. A tape T is attached to a second surface Wb opposite to the first surface Wa. The workpiece W is integrated with an annular frame F through the tape T. In the following, referring to the attached drawings, a description will be given of a non-destructive detection method of detecting, in a non-destructive manner, a modified layer formed by positioning a focal point of a laser beam of a wavelength transmissible through the workpiece W having the first surface Wa and the second surface Wb opposite thereto inside the workpiece W and applying the laser beam to the workpiece W.

(1) Preparation Step

As illustrated in FIG. 1, for example, an inspection apparatus 1 capable of forming a modified layer inside the workpiece W and imaging an inside of the workpiece W is prepared. The inspection apparatus 1 includes an apparatus base 10 and a column 11 with a substantially L-shaped cross-section erected on an upper surface of the apparatus base on a rear portion side in a Y-axis direction. The apparatus base 10 includes a holding table 12, frame holding means 15, an X-axis direction moving mechanism 20, and a Y-axis direction moving mechanism 30. The holding table 12 holds the workpiece W integrated with the frame F. The frame holding means 15 is disposed in a periphery of the holding table 12 to hold the frame F. The X-axis direction moving mechanism 20 causes the holding table 12 to move in the X-axis direction. The Y-axis direction moving mechanism 30 causes the holding table 12 to move in the Y-axis direction. A leading end of the column 11 is configured to extend to an upper side of a path in a moving direction (X-axis direction) of the holding table 12.

The holding table 12 has an upper surface serving as a holding surface 12*a* for holding the workpiece W thereon. The holding table 12 is fixed on a cover table 13 having an opening 130, and rotating means 14 is connected to a lower portion of the holding table 12. The rotating means 14 can rotate the holding table 12 at a predetermined angle.

The X-axis direction moving mechanism 20 includes a ball screw 21, an electric motor 22, a pair of guide rails 23, a bearing 24, and a moving base 25. The ball screw 21 extends in the X-axis direction. The electric motor 22 is connected to one end of the ball screw 21. The pair of guide rails 23 extends in parallel to the ball screw 21. The bearing 24 supports the other end of the ball screw 21 in a rotatable manner. The moving base 25 supports the holding table 12 through the Y-axis direction moving mechanism 30. The pair of guide rails 23 slides in contact with one face of the moving base 25, and the ball screw 21 is screwed into a nut formed at a center portion of the moving base 25. When the electric motor 22 rotates the ball screw 21, the moving base 25 moves along the pair of guide rails 23 in the X-axis direction, so that the holding table 12 can be moved in the X-axis direction.

The Y-axis direction moving mechanism 30 includes a ball screw 31, an electric motor 32, a pair of guide rails 33, a bearing 34, and a moving base 35. The ball screw 31 extends in the Y-axis direction. The electric motor 32 is connected to one end of the ball screw 31. The pair of guide rails 33 extends in parallel to the ball screw 31. The bearing 34 supports the other end of the ball screw 31 in a rotatable manner. The moving base 35 supports the holding table 12. The pair of guide rails 33 slides in contact with one face of the moving base 35, and the ball screw 31 is screwed into a nut formed at a center portion of the moving base 35. When the electric motor 32 rotates the ball screw 31, the moving base 35 moves along the pair of guide rails 33 in the Y-axis direction, so that a position of the holding table 12 in the Y-axis direction can be adjusted.

The inspection apparatus 1 includes laser processing means 40 subjecting the first surface Wa of the workpiece W held on the holding table 12 to laser processing. The laser processing means 40 is disposed on a lower portion side of the leading end of the column 11 and has a laser processing head 41 applying downward a laser beam 43 of a wavelength transmissible through the workpiece W illustrated in FIG. 2. The laser processing head 41 has a laser oscillator emitting the laser beam 43 and an output power adjuster adjusting an output power of the laser beam 43 connected thereto. Inside the laser processing head 41, a light condensing lens 42 for focusing the laser beam 43 emitted from the laser oscillator is incorporated. The laser processing head 41 is capable of moving in a vertical direction, so that a light focusing position of the laser beam 43 can be adjusted.

Herein, one example in which a modified layer is formed inside the workpiece W by the laser processing means 40 will be described. In the present embodiment, the following laser processing condition is set to be implemented, for example.

Figure 2:
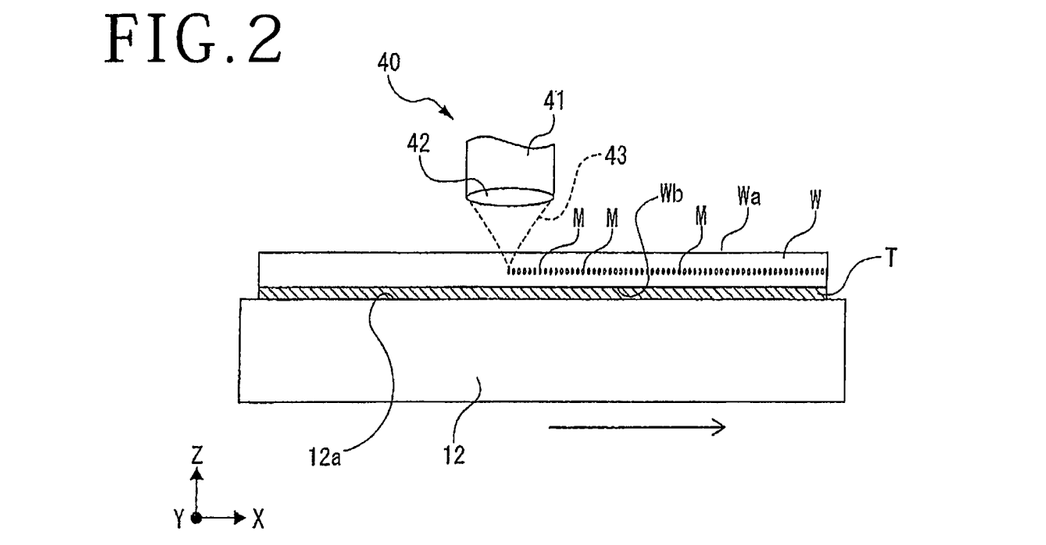
FIG. 2 is a cross-sectional view illustrating a state in which a modified layer is formed inside a workpiece.

[Laser Processing Condition]
  Wavelength of laser beam: 1064 nm
  Repetitive frequency: 50 kHz
  Average output power: 1.0 W
  Pulse width: 10 nm
  Focusing spot diameter: 3.0 μm
  Processing feed speed: 500 mm/s As illustrated in FIG. 2, with the Tape T side disposed downward on the holding surface 12*a* of the holding table 12, the workpiece W is sucked and held on the holding surface 12*a* of the holding table 12, after which the holding table 12 is moved below the laser processing means 40. Then, while the holding table 12 is processing-fed, for example, in the X-axis direction at a processing feed speed (500 mm/s) described above, in a state in which the light condensing lens 42 positions the light focusing point of the laser beam 43 of a wavelength transmissible through the workpiece W inside the workpiece W, the laser beam 43 is applied to the workpiece W along each of the division lines S illustrated in FIG. 1 from the first surface Wa side of the workpiece W. As a result, a modified layer M having a lower strength is formed inside the workpiece W.

In order to detect the modified layer M formed inside the workpiece W in a non-destructive manner, the inspection apparatus 1 illustrated in FIG. 1 includes imaging means 50, a light source 60, driving means 70, recording means 80, control means 90, and a monitor 100. The imaging means 50 includes an objective lens 52 (illustrated in FIG. 3) and images the workpiece W from the first surface Wa side of the workpiece W. The light source 60 emits a light of a wavelength band transmissible through the workpiece W from the first surface Wa side. The driving means 70 causes the objective lens 52 to move close to or apart from the first surface Wa. The recording means 80 records an image imaged by the imaging means 50. The control means 90 executes image processing based on the image recorded in the recording means 80. The monitor 100 causes various types of data (images, processing conditions, or the like) to be displayed thereon.

Figure 3:
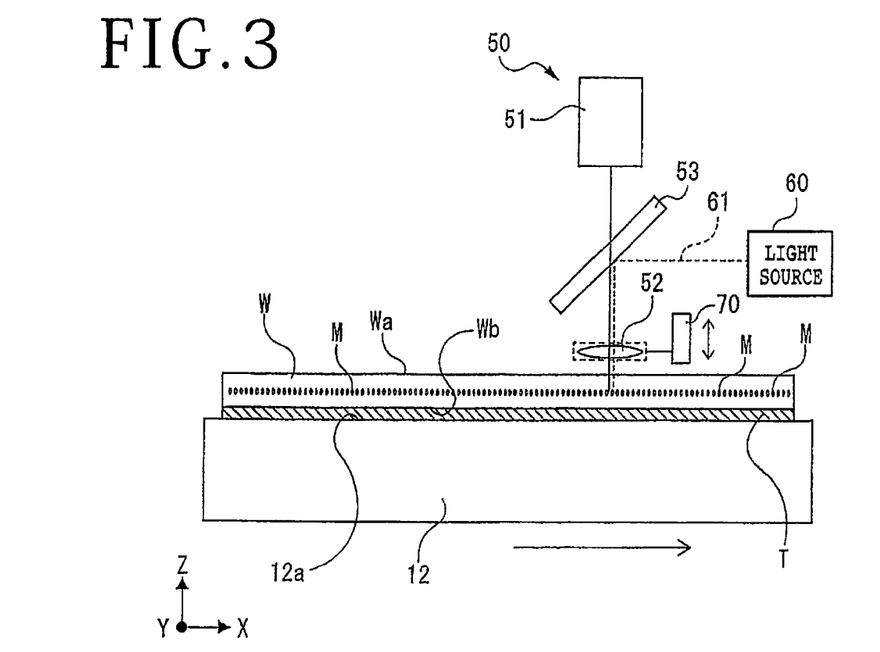
FIG. 3 is a cross-sectional view illustrating an image acquisition step.

The imaging means 50 is disposed in proximity to the laser processing means 40 on the lower portion side of the leading end of the column 11. As illustrated in FIG. 3, the imaging means 50 includes a camera 51, the objective lens 52, and a half mirror 53. The camera 51 images the workpiece W from above. The objective lens 52 is disposed at the lowermost portion of the camera 51. The half mirror 53 is disposed between the camera 51 and the objective lens 52 and causes light emitted from the light source 60 to reflect downward. The camera 51 is an infrared camera incorporating an imaging element such as a charge-coupled device (CCD) image sensor or a complementary metal-oxide semiconductor (CMOS) image sensor. The light source 60 includes, for example, an infrared light-emitting diode (LED) and can emit an infrared ray 61 of a wavelength band transmissible through the workpiece W. In the imaging means 50, a reflected light of the infrared ray 61 emitted from the light source 60 and reflected inside the workpiece W is captured by the imaging element, whereby it is possible to obtain an X-Y plane image defined in accordance with an X-axis coordinate and a Y-axis coordinate inside the workpiece W. The X-Y plane image imaged by the imaging means 50 is recorded in the recording means 80.

To the objective lens 52, the driving means 70 is connected. The driving means 70 is an actuator allowing the objective lens 52 to move up and down in the Z-axis direction. The driving means 70 includes a piezoelectric motor constituted of a piezoelectric element which expands and contracts in a vertical direction relative to the workpiece W held on the holding table 12 due to application of voltage, for example. The driving means 70 causes the objective lens 52 to move in upward and downward directions by adjusting a voltage applied to the piezoelectric element, so that a position of the objective lens 52 can be fine-adjusted. Accordingly, the driving means 70 moves the position of the objective lens 52 for each desired Z-axis coordinate value, and therefore, it is possible to image an X-Y plane image inside the workpiece W for each Z-axis coordinate value by the imaging means 50. Note that a configuration of the driving means 70 is not limited to the piezoelectric motor, and for example, a voice coil motor enabling a linear movement is applicable.

The control means 90 at least includes a central processing unit (CPU) which performs arithmetic processing according to a control program, an image processing section 91 which is connected to the CPU, a read only memory (ROM) which stores the control program or the like, a random access memory (RAM) which is capable of reading and writing and which stores a result of the arithmetic processing or the like, an input interface, and an output interface. In the image processing section 91 according to the present embodiment, it is possible to produce a three-dimensional image based on an X-Y plane image for each of plurality of Z-axis coordinate values recorded in the recording means 80.

In addition, the image processing section 91 can produce, for example, a sectional image (image cut in a direction parallel to the Z-axis direction) of the modified layer formed inside the workpiece W from the produced three-dimensional image. The X-Y plane image, the three-dimensional image, the sectional image of the modified layer obtained in this manner are displayed in the monitor 100, so that a state of the modified layer can be observed. Note that the control means 90 executes not only the image processing described above, but also controls each operation mechanism of the inspection apparatus 1.

(2) Image Acquisition Step

The inspection apparatus 1 is prepared, and the modified layer M is formed inside the workpiece W. After that, as illustrated in FIG. 3, while processing-feeding the holding table 12 in the X-axis direction, the imaging means 50 images a state of the inside of the workpiece W from the first surface Wa side of the workpiece W. In the image acquisition step illustrated in the present embodiment, with the first surface Wa of the workpiece W as the X-Y plane, a plurality of X-Y plane images parallel to the first surface Wa are imaged. It is assumed that a case in which the image acquisition step is carried out right after the modified layer M is formed along one column line of the division lines S oriented in the X-axis direction is described in the present embodiment.

Figure 4:
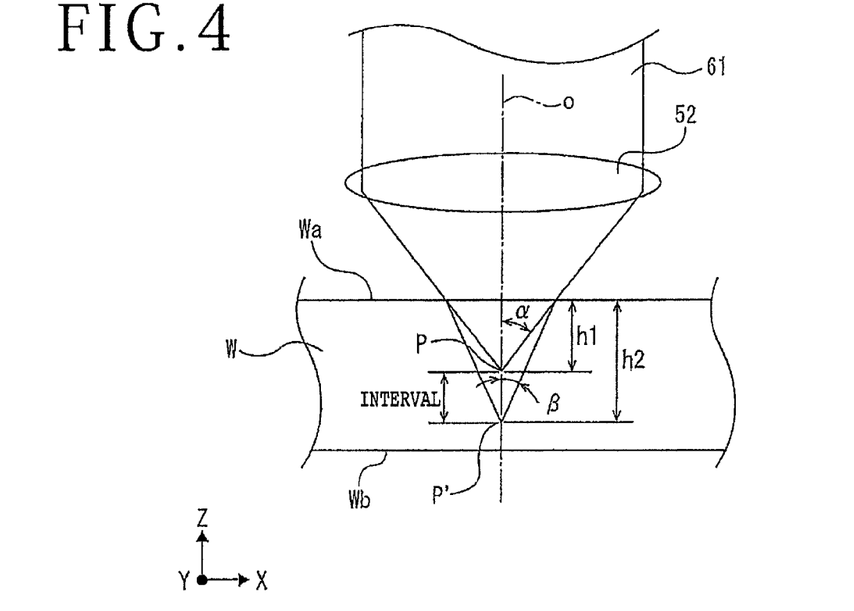
FIG. 4 is a schematic diagram illustrating a relation between a refractive index of the workpiece and a focal point of an objective lens.

In this step, the infrared ray 61 emitted from the light source 60 illustrated in FIG. 3 is reflected downward on the half mirror 53, and the reflected light passes through the objective lens 52 to enter the first surface Wa. At this time, an angle of refraction of the infrared ray 61 changes according to a refractive index (N) of the workpiece W. In other words, the refractive index (N) changes according to a type of a material of the workpiece W. FIG. 4 is a schematic diagram illustrating a relation between the refractive index (N) of the workpiece W and a focal point at which the infrared ray 61 is focused with the objective lens 52. For convenience of description, an angle α with respect to an optical axis O illustrated in the example of the figure indicates an angle in a case in which the infrared ray 61 passing through the objective lens 52 linearly enters the first surface Wa of the workpiece W without being refracted on the first surface Wa of the workpiece W, and in this case, a distance from the first surface Wa to a focal point P is set as a distance h1.

Normally, when the infrared ray 61 passing through the objective lens 52 enters the inside of the workpiece W from the first surface Wa of the workpiece W, the infrared ray 61 is refracted at an angle β, for example, from the angle α in the case in which the infrared ray 61 is not refracted, to be focused to a focal point P'. The angle β with respect to the optical axis O corresponds to the angle of refraction, and the refractive index (N) of the workpiece W in this case can be calculated based on the following equation (1) by Snell's law.

$$N = \sin\alpha / \sin\beta \qquad \text{equation (1)}$$

In addition, the refractive index (N) calculated by the above equation (1) is substituted to the following equation (2), whereby a distance h2 from the first surface Wa of the workpiece W to the focal point P' can be calculated by the equation (2).

$$h2 = N \times \cos \beta / \cos \alpha \times h1 \qquad \text{equation (2)}$$

The distance h2 is longer than the distance h1, and it is possible to confirm that a distance between the focal points (a distance between the focal point P and the focal point P') increases by a difference between the distance h2 and the distance h1. This difference in distance corresponds to a distance V of the focal point which lengthens within the workpiece in focusing the objective lens 52 for each of the plurality of Z-axis coordinate values.

When imaging the inside of the workpiece W, the driving means 70 causes the objective lens 52 to intermittently move by the predetermined distance H in the Z-axis direction orthogonal to the X-Y plane. Causing the objective lens 52 to intermittently move means that a position of the objective lens 52 is moved in the Z-axis direction with a fixed distance. The distance V of the focal point which lengthens within the workpiece W illustrated in an example of FIG. 5 changes depending on the refractive index (N) of the workpiece W to be inspected and a movement amount (H) of the objective lens 52 in the Z-axis direction; however, it is possible to obtain the predetermined distance V by multiplying the refractive index (N) calculated by the equation (1) described above by the movement amount (H) (V=N×H).

Figure 5:
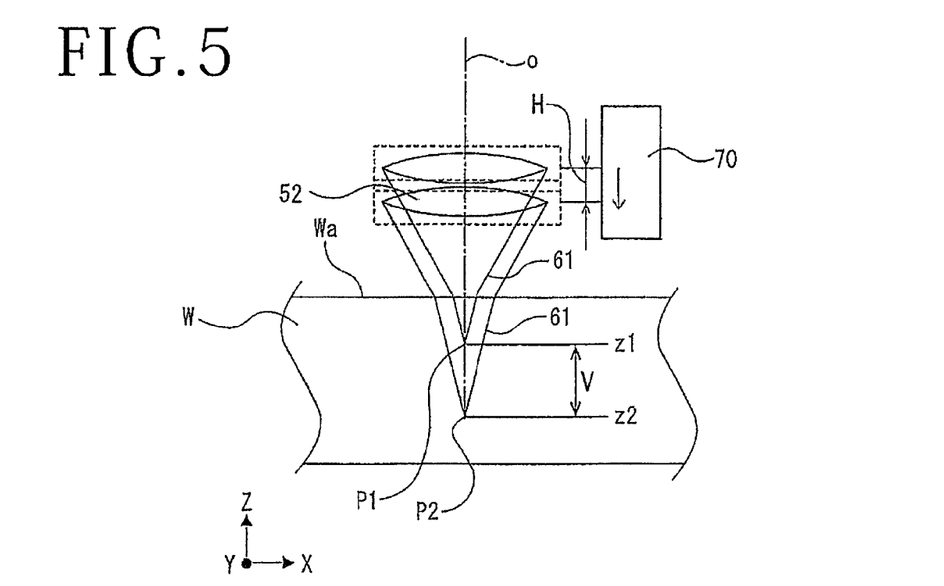
FIG. 5 is a schematic diagram for explanation of a state in which the objective lens is intermittently moved by a predetermined distance H in the image acquisition step.

In a case in which the workpiece W illustrated in the present embodiment is a silicon wafer, for example, the refractive index (N) thereof is 3.6. In a case in which the movement amount (V) by the driving means 70 is set to 1 μm, for example, by multiplying the refractive index (3.6) of the workpiece W by the movement amount (1 μm) of the objective lens 52, the resulting predetermined distance H can be calculated as 3.6 μm. In other words, a distance of the focal point extending inside the workpiece W (a distance between a Z-axis coordinate value z1 and a Z-axis coordinate value z2) becomes at least 3.6·H.

The driving means 70 causes the objective lens 52 to move downward in a direction approaching the first surface Wa of the workpiece W, thereby positioning a focal point P1 to the Z-axis coordinate value z1. When the inside of the workpiece W is imaged by the camera 51 illustrated in FIG. 3, for example, an X-Y plane image 2a illustrated in FIG. 6 can be obtained. Subsequently, the driving means 70 causes the objective lens 52 to intermittently move on the first surface Wa side in accordance with a setting of the distance V (3.6 μm) of the focal point which lengthens within the workpiece W described above and then, positions a focal point P2 to the Z-axis coordinate value z2 where a distance of the focal point P1 extends due to the refractive index (N) described above. When the camera 51 images the inside of the workpiece W, for example, an X-Y plane image 2b can be obtained. In this manner, the driving means 70 causes the position of the objective lens 52 to intermittently move by the predetermined distance H, and the inside of the workpiece W is imaged by the camera 51 for each of the Z-axis coordinate values z1, z2, . . . , so that the X-Y plane images 2a, 2b, 2c, 2d, 2e, 2f and 2g can be sequentially obtained. Then, the X-Y plane images 2a to 2g thus obtained are recorded in the recording means 80 illustrated in FIG. 1.

(4) Modified Layer Detecting Step

Figure 6:
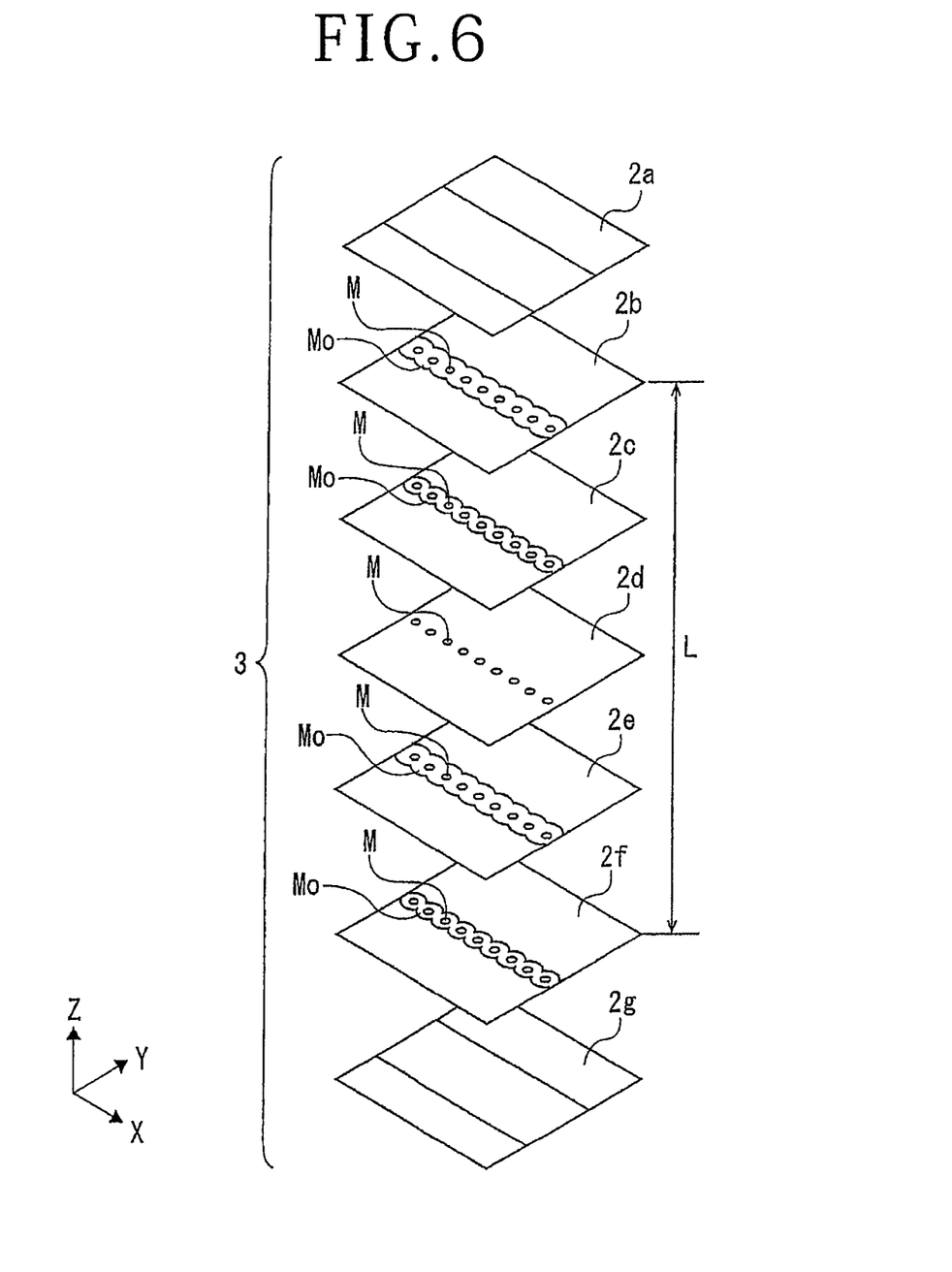
FIG. 6 is an image diagram of a three-dimensional image produced in a modified layer detecting step.

The image processing section 91 of the control means 90 illustrated in FIG. 1 three-dimensionally constructs the X-Y plane images 2a to 2g respectively corresponding to the plurality of Z-axis coordinate values z1 to z7 recorded in the recording means 80, thereby producing a three-dimensional image 3 illustrated in FIG. 6. The three-dimensional image 3 is displayed on the monitor 100. It can be confirmed that, in the three-dimensional image 3, the X-Y plane image 2a on the uppermost side and the X-Y plane image 2g on the lowermost side do not have the modified layer M reflected therein, while the X-Y plane images 2b to 2f each have the modified layer M reflected therein. In addition, although the X-Y plane images 2b to 2f each includes an out-of-focus portion Mo where the modified layer M gets blurred due to an influence of a slight error in a refractive portion, the out-of-focus portion Mo does not hinder detection of the modified layer M. More specifically, it is possible to detect the modified layer M by using the X-Y plane images from the X-Y plane image 2b in which the modified layer M including the out-of-focus portion Mo appears first to the X-Y plane image 2f in which the modified layer M including the out-of-focus portion Mo appears last.

Figure 7:
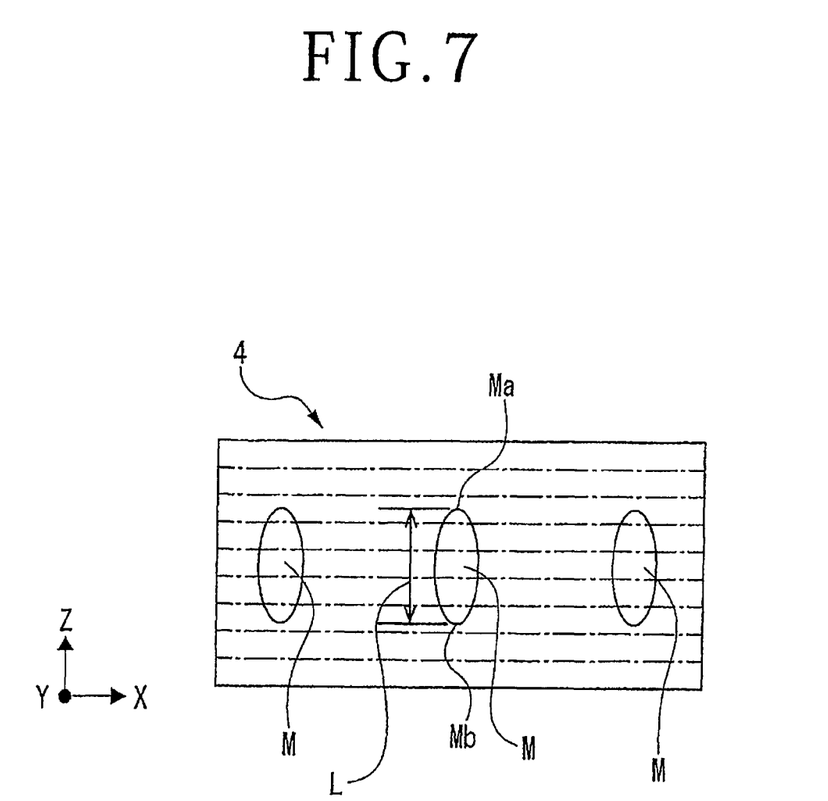
FIG. 7 is an image diagram of a two-dimensional image in which a modified layer cut in a direction parallel to a Z-axis direction based on the three-dimensional image is reflected.

The image processing section 91 produces a two-dimensional image 4 illustrated in FIG. 7, for example, as a sectional image appearing in a cross-section where the modified layer M is cut in a direction parallel to the Z-axis direction in the three-dimensional image 3. The two-dimensional image 4 is also displayed on the monitor 100. The modified layer M which is reflected in the two-dimensional image 4 is observed to thereby detect a depth position of the modified layer M in the Z-axis direction, a shape of the modified layer M, a length L from an upper end Ma to a lower end Mb of the modified layer M inside the workpiece W as a state of the modified layer M. In this manner, an entire shape of the modified layer M can be grasped by converting from the three-dimensional image 3 to the two-dimensional image 4, so that the state of the modified layer M can be detected with high precision. A detection result of the state of the modified layer M is stored in the RAM of the control means 90 to be used for selection of the most suitable laser processing condition.

Thus, in the non-destructive detection method according to the present invention, it is configured such that, after carrying out the preparation step of preparing the inspection apparatus 1 including the imaging means 50 provided with the objective lens 52 and imaging the workpiece W from the first surface Wa side, the light source 60 emitting light of a wavelength transmissible through the workpiece W from the first surface Wa side, the driving means 70 causing the objective lens 52 to move close to or apart from the first surface Wa, and the recording means 80 recording an image imaged by the imaging means 50, the image acquisition step of, for example, causing the objective lens 52 to intermittently move by the predetermined distance H in the Z-axis direction orthogonal to the X-Y plane to be made closer to the first surface Wa, positioning the focal point to the Z-axis coordinate value where the distance of the focal point extends by the refractive index of the workpiece W, acquiring the X-Y plane image inside the workpiece W for each of the plurality of Z-axis coordinate values, and recording the acquired X-Y plane image in the recording means 80, and the modified layer detecting step of detecting the state of the modified layer M from the X-Y plane images 2a to 2g for each of the plurality of Z-axis coordinate values recorded in the recording means 80 are carried out. As a result, it is possible to detect the state of the modified layer M without destructing the workpiece W. Accordingly, according to the present invention, it is possible to repetitively carry out formation of the modified layer M by laser processing and detection of the state of the modified layer M by the imaging means 50, and the most suitable laser processing condition for forming a desired modified layer M can be quickly selected.

Note that the inspection apparatus 1 illustrated in the present embodiment is configured so as to function as a laser processing apparatus which forms the modified layer M inside the workpiece W; however, the inspection apparatus 1 is not limited to the apparatus configuration illustrated in the present embodiment and may have an apparatus configuration in which the inspection apparatus 1 is a single apparatus independent of a laser processing apparatus.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A non-destructive detection method of detecting, in a non-destructive manner, a modified layer formed by positioning, inside a workpiece having a first surface and a second surface opposite to the first surface, a focal point of a laser beam of a wavelength transmissible through the workpiece and applying the laser beam to the workpiece, the method comprising:

a preparing step of preparing an inspection apparatus including imaging means provided with an objective lens and imaging the workpiece from a side of the first surface, a light source emitting light of a wavelength band transmissible through the workpiece from the side of the first surface, driving means causing the objective lens to move close to or apart from the first surface, and recording means recording an image imaged by the imaging means;

an image acquisition step of, in a case in which the first surface is set as an X-Y plane, intermittently moving the objective lens by a predetermined distance H in a Z-axis direction orthogonal to the X-Y plane to be made closer to the first surface, positioning the focal point to each of a plurality of Z-axis coordinate values where a distance of the focal point extends by a refractive index of the workpiece, acquiring an X-Y plane image of an inside of the workpiece for each of the plurality of Z-axis coordinate values, and then, recording the acquired images in the recording means; and a modified layer detecting step of detecting a state of the modified layer from the X-Y plane image for each of the plurality of Z-axis coordinate values recorded in the recording means.

2. The non-destructive detection method according to claim 1, wherein in the modified layer detecting step, a three-dimensional image is produced from the X-Y plane image for each of the plurality of Z-axis coordinate values recorded in the recording means, and from a two-dimensional image appearing in a cross-section where the modified layer is cut in a direction parallel to the Z-axis direction, a depth position of the modified layer in the Z-axis direction and a shape of the modified layer are detected as the state of the modified layer.

3. The non-destructive detection method according to claim 1, wherein the workpiece is a silicon wafer having a refractive index of 3.6, and in the image acquisition step, the distance of the focal point which extends inside the workpiece with respect to the predetermined distance H at which the objective lens intermittently moves in the Z-axis direction is at least $3.6 \cdot H$, and the focal point intermittently moves by $3.6 \cdot H$ inside the workpiece.

* * * * *